(12) United States Patent
Mannanal et al.

(10) Patent No.: US 10,368,913 B2
(45) Date of Patent: Aug. 6, 2019

(54) ADJUSTMENT INSTRUMENT WITH TACTILE FEEDBACK

(71) Applicant: Stryker European Holdings I, LLC, Kalamazoo, MI (US)

(72) Inventors: Subash K. Mannanal, Mahwah, NJ (US); Daniel Greenberg, Ramsey, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 159 days.

(21) Appl. No.: 15/180,530

(22) Filed: Jun. 13, 2016

(65) Prior Publication Data

US 2017/0042580 A1    Feb. 16, 2017

Related U.S. Application Data

(60) Provisional application No. 62/203,176, filed on Aug. 10, 2015.

(51) Int. Cl.
  *A61B 17/00* (2006.01)
  *A61B 17/66* (2006.01)
  (Continued)

(52) U.S. Cl.
  CPC .............. *A61B 17/66* (2013.01); *A61B 17/62* (2013.01); *A61B 17/645* (2013.01); *A61B 17/8894* (2013.01); *A61B 2017/564* (2013.01)

(58) Field of Classification Search
  CPC ............ A61B 17/8872; A61B 17/8875; A61B 17/60–666
  See application file for complete search history.

(56) References Cited

U.S. PATENT DOCUMENTS 4,365,624 A    12/1982 Jaquet
4,570,625 A    2/1986 Harris et al.
(Continued)

FOREIGN PATENT DOCUMENTS

EP    2252222 A1    11/2010

OTHER PUBLICATIONS

Extended European Search Report for Application No. 16179304.7 dated Dec. 8, 2016.
(Continued)

*Primary Examiner* — Nicholas J Plionis
*Assistant Examiner* — Steven J Cotroneo
(74) *Attorney, Agent, or Firm* — Lerner, David, Littenberg, Krumholz & Mentlik, LLP

(57) ABSTRACT

An external fixation frame system may include a first ring, a second ring, and at least three struts configured to couple the first ring to the second ring, each strut having a rotatable head portion and a counter torque portion. The system may also include an adjustment tool that includes a driver portion having an inner engagement portion for engaging the head portion of the strut, an outer engagement portion for engaging the counter torque portion of the strut, and a feedback mechanism rotatably coupled to the inner and outer engagement portions. The tool may further include a plunger having an inner portion positioned at least partially within the inner engagement portion, and an outer portion positioned at least partially between the inner engagement portion and the outer engagement portions, the plunger being axially translatable with respect to the inner and outer engagement portions.

14 Claims, 8 Drawing Sheets

(51) Int. Cl.
*A61B 17/88* (2006.01)
*A61B 17/62* (2006.01)
*A61B 17/64* (2006.01)
*A61B 17/56* (2006.01)

(56) References Cited

U.S. PATENT DOCUMENTS

| | | | |
|---|---|---|---|
| 4,615,338 A | | 10/1986 | Ilizarov et al. |
| 4,973,331 A | | 11/1990 | Pursley et al. |
| 4,978,348 A | | 12/1990 | Ilizarov |
| 5,014,794 A | | 5/1991 | Hansson |
| 5,108,393 A | | 4/1992 | Ruffa |
| 5,108,394 A | | 4/1992 | Kurokawa et al. |
| 5,156,605 A | | 10/1992 | Pursley et al. |
| 5,180,380 A | | 1/1993 | Pursley et al. |
| 5,334,202 A | | 8/1994 | Carter |
| 5,437,668 A | | 8/1995 | Aronson et al. |
| 5,702,389 A | | 12/1997 | Taylor et al. |
| 5,788,695 A | | 8/1998 | Richardson |
| 5,971,984 A | | 10/1999 | Taylor et al. |
| 6,017,354 A | | 1/2000 | Culp et al. |
| 6,033,412 A | | 3/2000 | Losken et al. |
| 6,132,435 A | * | 10/2000 | Young ................ A61B 17/8875 192/56.54 |
| 7,243,581 B1 | * | 7/2007 | Gao ..................... B25B 23/141 192/38 |
| 7,272,998 B1 | * | 9/2007 | Gauthier ............... B25B 23/141 81/473 |
| 7,559,951 B2 | | 7/2009 | DiSilvestro et al. |
| 7,955,334 B2 | | 6/2011 | Steiner et al. |
| 8,157,800 B2 | | 4/2012 | Vvedensky et al. |
| 8,167,880 B2 | | 5/2012 | Vasta |
| 8,282,652 B2 | | 10/2012 | Mackenzi et al. |
| 8,333,766 B2 | | 12/2012 | Edelhauser et al. |
| 8,702,705 B2 | | 4/2014 | Ziran et al. |
| 8,714,056 B2 | * | 5/2014 | Landowski ......... B25B 23/1427 81/474 |
| 8,864,750 B2 | | 10/2014 | Ross et al. |
| 9,511,484 B2 | * | 12/2016 | Marchant ................ B25B 15/04 |
| 9,987,066 B2 | * | 6/2018 | Stad .................... A61B 17/8886 |
| 2002/0010465 A1 | | 1/2002 | Koo et al. |
| 2003/0149378 A1 | | 8/2003 | Peabody et al. |
| 2003/0191466 A1 | | 10/2003 | Austin et al. |
| 2003/0199856 A1 | | 10/2003 | Hill et al. |
| 2005/0215997 A1 | | 9/2005 | Austin et al. |
| 2006/0207118 A1 | | 9/2006 | Kim |
| 2007/0085496 A1 | | 4/2007 | Philipp et al. |
| 2007/0225704 A1 | | 9/2007 | Ziran et al. |
| 2007/0233134 A1 | | 10/2007 | Bastian et al. |
| 2008/0178713 A1 | | 7/2008 | Long et al. |
| 2008/0243134 A1 | * | 10/2008 | Limberg ............ A61B 17/8875 606/104 |
| 2008/0281332 A1 | | 11/2008 | Taylor |
| 2010/0121323 A1 | | 5/2010 | Pool et al. |
| 2010/0264864 A1 | | 10/2010 | Hafner et al. |
| 2011/0004199 A1 | | 1/2011 | Ross et al. |
| 2012/0041439 A1 | * | 2/2012 | Singh .................... A61B 17/62 606/54 |
| 2012/0109143 A1 | | 5/2012 | Steele et al. |
| 2012/0330312 A1 | | 12/2012 | Burgherr et al. |
| 2013/0253513 A1 | | 9/2013 | Ross et al. |
| 2013/0289575 A1 | | 10/2013 | Edelhauser et al. |
| 2014/0236153 A1 | | 8/2014 | Edelhauser |
| 2014/0277203 A1 | | 9/2014 | Atoulikian et al. |
| 2015/0045840 A1 | * | 2/2015 | Vaucher ............. A61B 17/1728 606/305 |

OTHER PUBLICATIONS

European Search Report for Application No. 15190728.4 dated Mar. 30, 2016.

\* cited by examiner

ADJUSTMENT INSTRUMENT WITH TACTILE FEEDBACK

CROSS-REFERENCE TO RELATED APPLICATIONS

This application claims the benefit of the filing date of U.S. Provisional Application No. 62/203,176 filed Aug. 10, 2015, the disclosure of which is hereby incorporated by reference herein.

BACKGROUND OF THE DISCLOSURE

The present disclosure relates to methods, tools, and systems for adjusting an external fixation frame. More particularly, the present disclosure relates to methods, tools, and systems for repositioning the components of an external fixation frame according to a correction plan.

The external fixation market can be divided into two major segments: acute trauma and reconstructive. The trauma segment generally includes modular fixators having fewer components and structured for rapid application to a patient. These frames may be used for temporizing fixation and may only be on the patient for hours or days.

The reconstructive segment includes ring fixators, such as the Ilizarov frame, for example. Such frames are shown in U.S. Pat. Nos. 4,365,624, 4,615,338, 4,978,348, 5,702,389, and 5,971,984. Ring fixators may be used with a combination of pins and wires to achieve a variety of polyaxial pin/wire attachments that provide stability. They can achieve a full six degrees of freedom and can correct primary deformities without creating secondary deformities. Rotational deformities may also be treated with ring fixators. However, mastery of the techniques involved with using ring fixators, as well as the products themselves, can be a long and daunting process.

At times, it may be necessary to realign, reposition, and/or securely hold two bone elements relative to one another. For example, in the practice of medicine, bone fragments and the like are sometimes aligned, realigned, and/or repositioned to restore boney continuity and skeletal function. At times, this may be accomplished by sudden maneuver, followed by skeletal stabilization with cast, plate and screws, intramedullary devices, or external skeletal fixators.

A bone fragment can be moved, in general, from its original position as in a nonunion or malunion or from its intended position as in congenital deformities along six separate movements or degrees of freedom, a combination of three orthogonal translational axes (e.g., typical "X," "Y" and "Z" axes) and three orthogonal rotational axes (e.g., rotation about such typical "X," "Y" and "Z" axes).

External fixation devices may be attached to the boney skeleton with threaded and/or smooth pins and/or threaded and/or smooth and/or beaded wires. Such constructs may be referred to as orthopaedic external fixators or external skeletal fixators. External fixators may be utilized to treat acute fractures of the skeleton, soft tissue injuries, delayed union of the skeleton when bones are slow to heal, nonunion of the skeleton when bones have not healed, malunion whereby broken or fractures bones have healed in a malposition, congenital deformities whereby bones develop a malposition, and bone lengthening, widening, or twisting.

A circumferential external fixator system was disclosed by G. A. Ilizarov during the early 1950s. The Ilizarov system includes at least two rings or "halos" that encircle a patient's body member (e.g., a patient's leg), connecting rods extending between the two rings, transfixation pins that extend through the patient's boney structure, and connectors for connecting the transfixation pins to the rings.

Often, orthopaedic external fixators such as Ilizarov fixators are repositioned after their initial application. Such modification may help convert from one correctional axis to another or to convert from an initial adjustment type of fixator to a weight bearing type of fixator, some of the correctional configurations not being stable enough for weight bearing.

As discussed above, most external fixators should be adjusted over a period of time to reposition bone segments. The adjustment of the external fixation may be implemented according to a "prescription" or correction plan. Physicians may adjust the external fixator at precise times over a period of time (e.g, on a daily basis for three weeks). Patients, however, may not desire to visit the physician's office every time an adjustment is needed. For this reason, external fixators may be adjusted by the patients themselves, at his or her home, for example, without the assistance of a physician. The adjustment of the external fixator should nonetheless strictly comply with the predetermined correction plan. For the foregoing reasons, it is desirable to provide a tool, system, and/or method for helping a patient implement a correction plan in an external fixator.

BRIEF SUMMARY

According to one aspect of the disclosure, a tool for actuating one or more of a plurality of struts of an external fixation frame includes a handle portion and a driving portion operably coupled to the handle portion. The driving portion may have an inner engagement portion configured to couple to a movable portion of each of the struts, an outer engagement portion configured to couple to a non-movable portion of each of the struts, and a feedback mechanism operably coupled to the inner and outer engagement portions. The inner engagement portion is movable with respect to the outer engagement portion, and the feedback mechanism is movable with respect to both the inner and outer engagement portions. The movable portion of each strut may be a rotatable portion, and the feedback mechanism may be rotatable with respect to both the inner and outer engagement portions. The tool may also include a plunger having an inner portion positioned at least partially within the inner engagement portion, and an outer portion positioned at least partially between the inner engagement portion and the outer engagement portions, the plunger being axially translatable with respect to the inner and outer engagement portions. The feedback mechanism may have a first mating structure and the outer portion of the plunger may have a second mating structure corresponding to the first mating structure. The plunger may have a first axial position in which the first mating structure is disengaged with the second mating structure, and a second axial position in which the first mating structure is engaged with the second mating structure, the plunger being rotationally fixed with respect to the feedback mechanism when the plunger is in the second axial position. The outer engagement portion may include at least one ball detent mechanism and the feedback mechanism may include a plurality of recesses configured to engage the at least one ball detent mechanism. The first mating structure of the feedback mechanism and the second feedback structure of the outer portion of the plunger may both be grooves.

According to another aspect of the disclosure, an external fixation frame system includes a first ring, a second ring, and at least three struts configured to couple the first ring to the second ring, each strut having a rotatable head portion and a counter torque portion. The system may also include an adjustment tool that includes a driver portion having an inner engagement portion for engaging the head portion of the strut, an outer engagement portion for engaging the counter torque portion of the strut, and a feedback mechanism rotatably coupled to the inner and outer engagement portions. The tool may be devoid of motors and electronic components. The tool may further include a plunger having an inner portion positioned at least partially within the inner engagement portion, and an outer portion positioned at least partially between the inner engagement portion and the outer engagement portions, the plunger being axially translatable with respect to the inner and outer engagement portions. The feedback mechanism may have a first mating structure and the outer portion of the plunger may have a second mating structure corresponding to the first mating structure. The plunger may have a first axial position in which the first mating structure is disengaged with the second mating structure, and a second axial position in which the first mating structure is engaged with the second mating structure, the plunger being rotationally fixed with respect to the feedback mechanism when the plunger is in the second axial position. The outer engagement portion may include at least one ball detent mechanism and the feedback mechanism may include a plurality of recesses configured to engage the at least one ball detent mechanism. The first mating structure of the feedback mechanism and the second feedback structure of the outer portion of the plunger may both be grooves.

According to a further aspect of the disclosure, a method for implementing a correction plan in an external fixation frame having at least two fixation rings and a plurality of struts coupling the at least two fixation rings includes certain steps. One step may be engaging an inner engagement portion of an adjustment tool to a head of one of the struts, with another step being engaging an outer engagement portion of the adjustment tool to a counter torque component of the strut. The method may further include rotating the adjustment tool to rotate the strut, wherein the outer engagement portion of the tool remains rotationally fixed with respect to the counter torque component, and a feedback mechanism of the tool rotates with respect to the outer engagement portion, while the inner engagement portion causes rotation of the strut. The feedback mechanism may provide at least one of audible and tactile feedback to the user as the feedback mechanism rotates with respect to the outer engagement portion. The step of engaging the inner engagement portion of the adjustment tool to the head of the strut may include driving a plunger positioned at least partially within the inner engagement portion from a first axial position to a second axial position, the plunger frictionally engaging the feedback mechanism when in the second axial position. The frictional engagement of the plunger and the feedback mechanism may be caused by grooves on an outer surface of the plunger engaging with corresponding grooves on an inner surface of the feedback mechanism. Rotation of the feedback mechanism with respect to the outer engagement portion may cause a ball detent at least partially within the outer engagement portion to disengage with a first recess in the feedback mechanism. The step of engaging the inner engagement portion of the adjustment tool to the head of the strut may be performed prior to the step of engaging the outer engagement portion of the adjustment tool to the counter torque component of the strut, the outer engagement portion of the tool being free to rotate just prior to engaging the counter torque component.

BRIEF DESCRIPTION OF THE DRAWINGS

Various embodiments of the present disclosure will now be described with reference to the appended drawings. It is appreciated that these drawings depict only some embodiments of the invention and are therefore not to be considered limiting of its scope.

DETAILED DESCRIPTION

Figure 1:
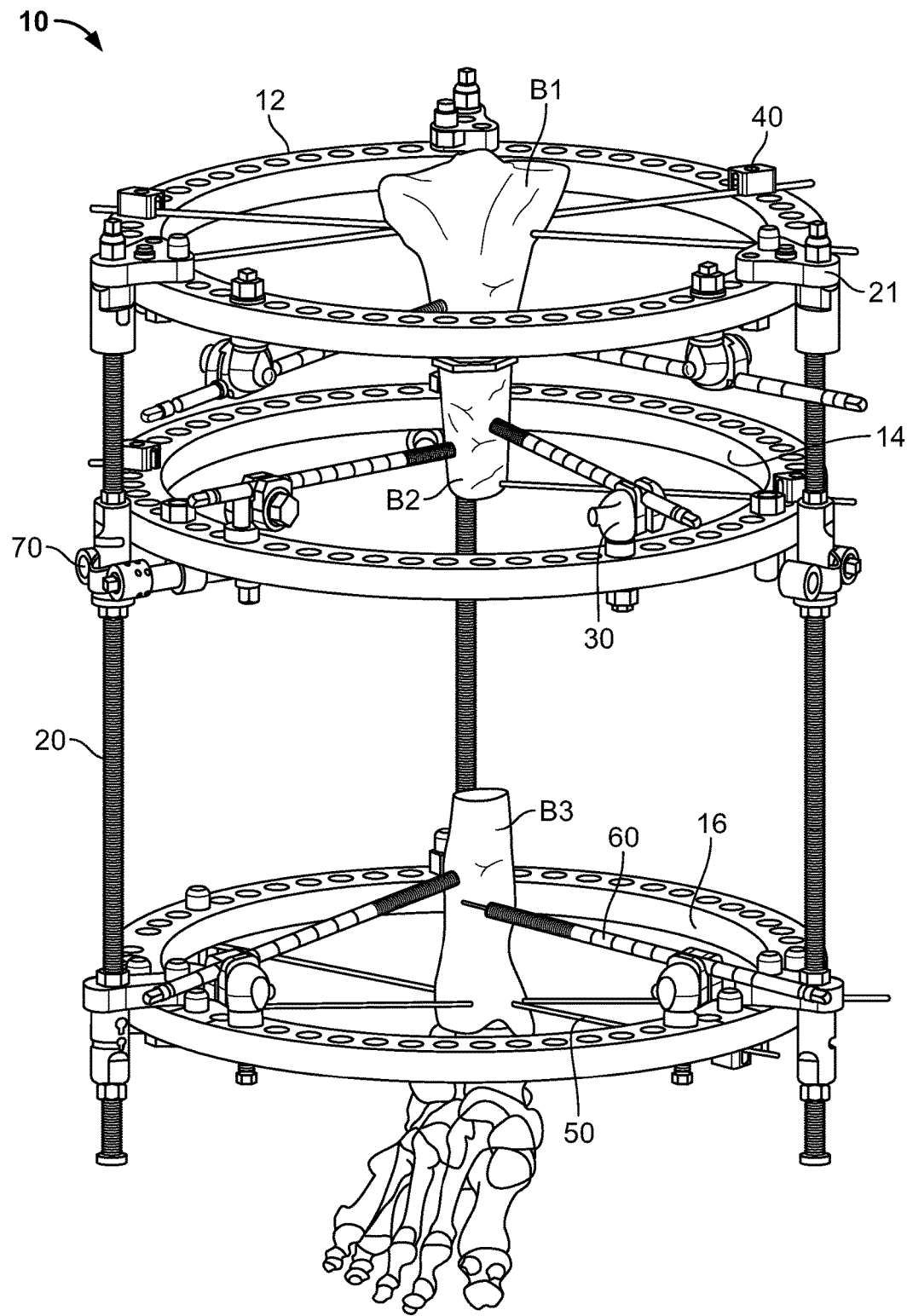
FIG. 1 is an isometric view of an external fixation frame.

The present disclosure describes in detail embodiments of methods and systems for adjusting an external fixation frame with reference to the drawings in which like reference numerals designate identical or substantially similar parts in each view. As used herein, "clinician" refers to a physician, surgeon, nurse or other care provider and may include support personnel. Also, as used herein, when the term "distal" is used with reference to a device, the term refers to a location relatively far away from a user of the device, while the term "proximal" refers to a location relatively close to the user.

FIG. 1 illustrates an embodiment of an external fixation frame 10. The fixation frame 10 generally includes a first ring 12, a second ring 14, and a third ring 16 coupled to one another via a plurality of struts 20.

Along the circumference of each of the rings 12, 14, resides a plurality of through-holes that extend through the upper and lower ring surfaces. The through-holes facilitate mechanical connections between the rings and the struts 20, as well as between the rings and other devices the surgeon may deem necessary during use of fixation frame 10.

Such devices, for example, include bone-pin retaining devices 30 and bone-wire retaining devices 40. Due to the substantially flat contours of the ring surfaces and the plurality of through-holes, a user is provided significant flexibility in appropriately placing the bone-pin retaining devices 30 and bone-wire retaining devices 40 at desired locations. Thus, a user can couple any of these devices at numerous locations around the circumference of each of the rings 12, 14, 16 as well as coupling the devices at the upper or lower ring surfaces of the rings. Devices that can be used to facilitate interaction between the fixation frame 10 and portions of a bone B1 B2, B3 include, for example, a series of bone-wires 50 and bone-pins 60.

As shown in FIG. 1, fixation frame 10 includes a proximal ring 12 affixed to a first bone segment B1, a medial ring 14 affixed to a second bone segment B2, and a distal ring 16 affixed to a third bone segment B3. The first bone segment B1 and second bone segment B2 are typically separated by an osteotomy created in the bone to allow for osteogenesis as the second bone segment is incrementally transported toward the third bone segment B3. The second bone segment B2 and third bone segment B3 are typically separated by a deformity, such as a fracture or the like.

Struts 20 act to stabilize the bone segments and to provide for transportation thereof. Although three struts 20 are shown, other fixation frames may have more struts, such as six struts. Additionally, although struts 20 do not change length, other fixation frames include telescoping struts that can change length, as is typically seen in fixation frames with two rings. The tool described below is compatible with both types of struts.

Each strut 20 may be coupled to one or more rings via a flange 21, for example with a pin extending through a hole of the flange and into a through-hole of the ring. Strut 20 may include a head that may be rotated with a tool, the rotation of the head causing the rotation of the threads of the strut 20. In the illustrated fixation frame 20, rotation of the struts 20 causes medial ring 14 to move up toward proximal ring 12, or down toward distal ring 15, depending on the direction of rotation. Also in this particular embodiment, medial ring 14 may be coupled to struts 20 via joints 70 which allow for some amount of rotation of the medial ring 14 so that ring 14 is no longer parallel to rings and 16. In other external fixation frames, a similar rotation of a head causes a threaded portion of the strut to advance into or extend out of a generally cylindrical shaft in a telescoping fashion to increase or decrease the total length of the strut, therefore moving rings attached to the ends of the strut closer or farther apart. Struts 20, and particularly the interaction of struts 20 with the tool of the present disclosure, is described in greater detail below.

Figure 2:
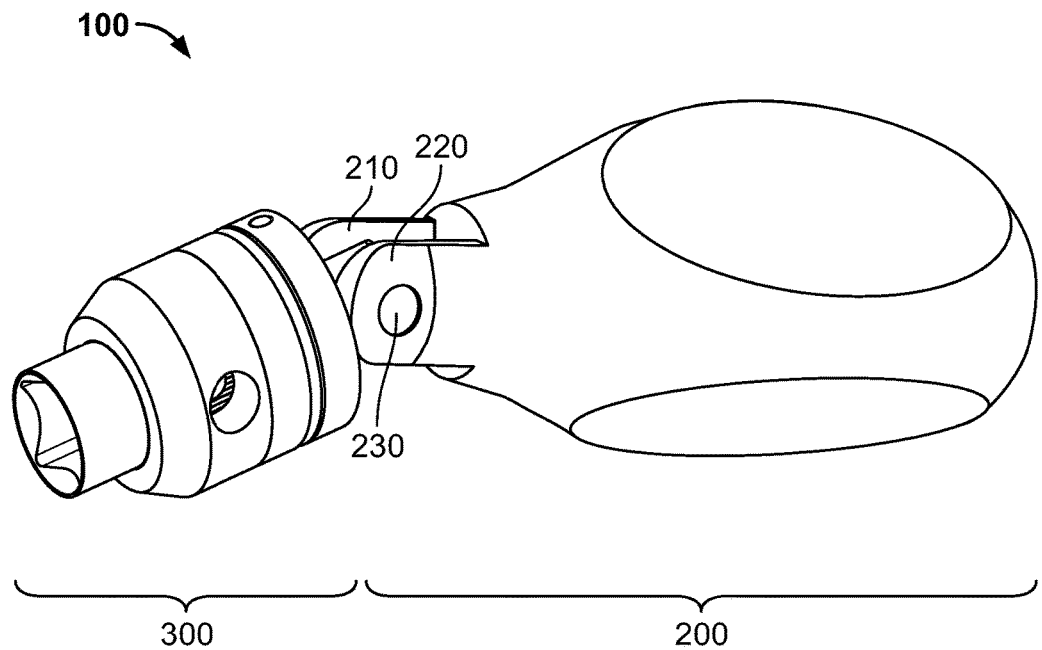
FIG. 2 is a perspective view of a manual driving tool according to an aspect of the disclosure.

FIG. 2 illustrates a perspective view of a tool 100 for adjusting struts 20 of fixation frame 10, although it should be understood that the tool may be used with other types of struts, such as telescoping struts, or other types of fixation frames. Tool 100 includes a handle portion 200 and a driver portion 300. Handle portion 200 may be coupled to driver portion 300 by any suitable mechanism that transfers torque. In the illustrated embodiment, a distal end of handle portion 200 includes two flanges 210, 220 spaced apart from one another. A proximal end of driver portion 300 may include a transverse pin 230 extending into through-holes in flanges 210, 220. With this configuration, handle portion 200 may pivot with respect to driver portion 300 about transverse pin 230, while torque applied to handle portion 200 is transmitted to driver portion 300.

Figure 3:
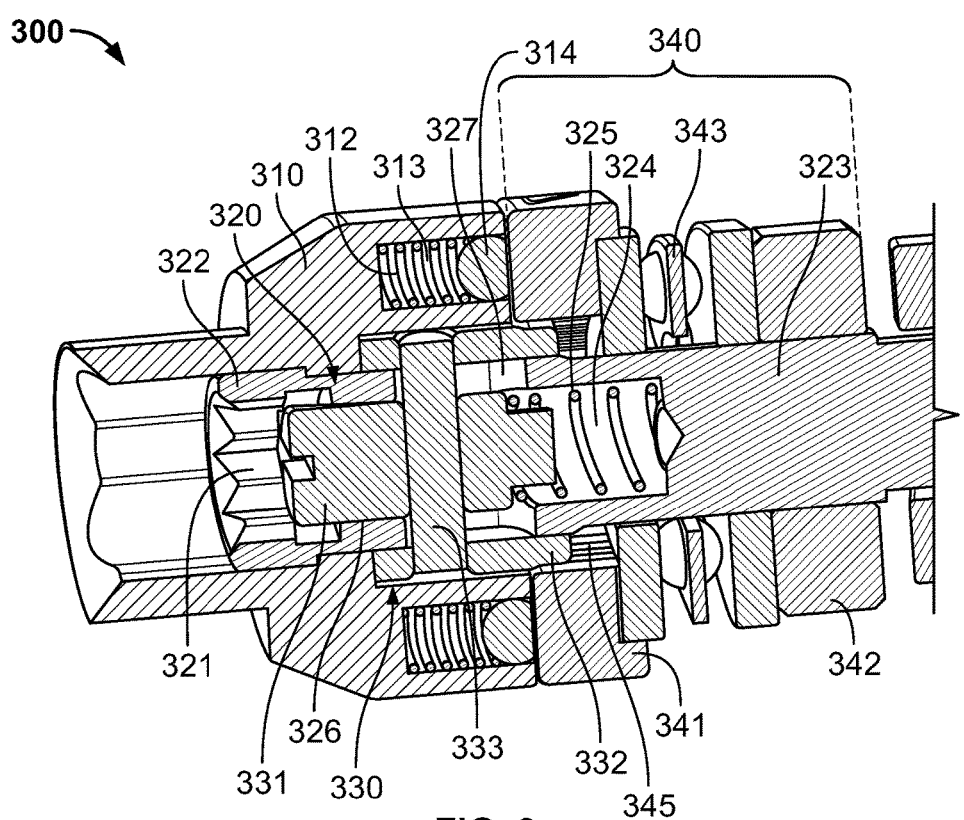
FIG. 3 is a cross-section of a driving portion of the tool of FIG. 2 in an unengaged position.

A cross-section of driver portion 300 is shown in greater detail in FIG. 3. Generally, driver portion 300 includes an outer engagement portion 310, an inner engagement portion 320, a plunger portion 330, and a clicking mechanism portion 340. Outer engagement portion 310 serves to couple to a counter torque/anti-rotation component of strut 20, while inner engagement portion 320 serves to couple to a head 23 of strut 20 that causes rotation, and thus adjustment of fixation frame 10 (and also adjustment of the strut length in the case of telescopic struts). A proximal end of inner engagement portion 320 is coupled to handle via transverse pin 230, as described above. Plunger portion 330 serves to assist clicking mechanism portion 340 in rotating with respect to outer engagement portion 310 to track rotation when the driver portion 300 is engaged with the strut 20. Clicking mechanism portion 340 serves to provide feedback to the user regarding the degree to which tool 100 rotates strut 20, as well as to track the rotation.

Outer engagement portion 310 may be generally cylindrical with a relatively narrow distal portion that is configured to mate with strut 20, as described in greater detail below. A proximal end of outer engagement portion 310 may include a plurality of cylindrical recesses 312 positioned at substantially equal intervals around the outer circumference of the proximal end of outer engagement portion 310. One or more of the cylindrical recesses 312 may include a spring 313 and ball 314 positioned at the end of the spring, so that the spring tends to force the ball toward the proximal opening in the recess 312.

Figure 7:
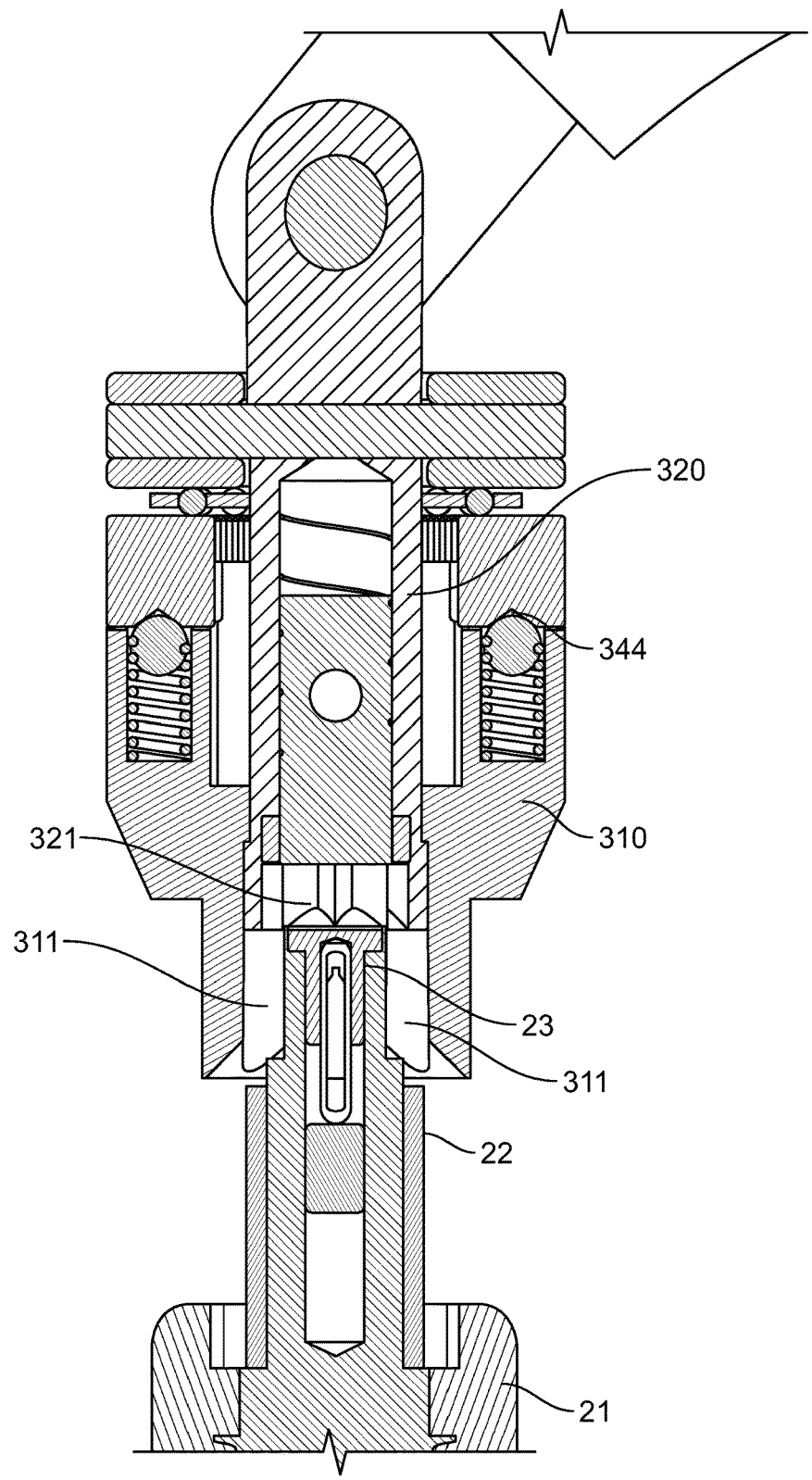
FIG. 7 is a cross-section of the tool of FIG. 2 engaged with the strut of FIG. 4 in an initial engagement position.

Clicking mechanism portion 340 includes distal clicking portion 341 and proximal portion 342, with bearings 343 positioned between the distal and proximal portions. A plurality of recesses 344 or notches as best seen in FIG. 7, for example, are positioned at substantially equal intervals around the outer circumference of the distal end of distal clicking portion 341, preferably with one recess 344 corresponding to each cylindrical recess 312. With this configuration, outer engagement portion 310 may be rotated with respect to distal clicking portion 341 in discrete intervals. In other words, when cylindrical recesses 312 align with recesses 344, the springs 313 in each cylindrical recess push a corresponding ball 314 into a corresponding recess 344. When in this condition, the interaction between each ball 314 and corresponding recess 344 provides resistance against rotation of distal clicking portion 341 with respect to outer engagement portion 310. This resistance may be overcome with intentional torqueing of the distal clicking portion 341 with respect to the outer engagement portion 310. With the resistance overcome, distal clicking portion 341 rotates with respect to outer engagement portion 310 until the recesses 344 align with the cylindrical recesses 312 in another configuration. When the recesses 344 align with corresponding cylindrical recesses 312, the springs 313 force the balls 314 into corresponding recesses 344, which may result in an audible "clicking" sound and/or tactile feedback to notify the user that the balls 314 have engaged the recesses 344. With this configuration, each time the balls 314 engage the corresponding recesses 344, the user is informed that the distal clicking portion 341 has rotated a known value with respect to outer engagement portion 310. This, in turn, may notify the user that the strut 20 has rotated a particular amount (or in the case of telescopic struts, increased or decreased a particular distance). In one example, outer engagement portion 310 may include eight recesses 312 and distal clicking portion 341 may include eight corresponding recesses 344. Two springs 313 and balls 314 may be positioned in diametrically opposite recesses 312, although more may be used if desired. With this configuration, each "click" indicates a ⅛ rotation of strut 20, which may correspond to approximately ⅛ millimeter axial advancement of the strut.

Distal clicking portion 341 may include a plurality of grooves 345 running along the inner circumference, which may engage corresponding grooves of plunger portion 330, described in greater detail below. The use of distal clicking portion 341 to keep track of particular adjustments of a fixation frame and corresponding struts 20 is described in greater detail below. Proximal portion 342 of clicking mechanism portion 340 may be rotationally coupled to inner engagement portion 320 by a pin extending through inner engagement portion 320 and into a recess in the proximal portion 342. Proximal portion 342 acts to help ensure that distal portion 341 stays in contact with balls 314 despite the forces supplied by springs 313. Proximal portion 342 preferably is rotationally fixed with respect to distal portion 341, with the bearings 343, which may be for example ball bearings, acting to reduce friction between the proximal and distal portions.

Inner engagement portion 320 may generally include two portions or sections, namely a distal section 322 and a proximal section 323. Distal section 322 may include an eight-pointed star cavity 321, described in greater detail below in connection with FIG. 5. Proximal section 323 of inner engagement portion 320 may extend toward handle portion 200 and be situated between flanges 210, 220 as described above. A distal end of proximal section 323 may define a recess 324, and a biasing member such as a spring 325 may be positioned within recess 324, which may be generally cylindrical. Distal section 322 may also include a recess 326 having a similar shape. Distal section 322 and proximal section 323 of inner engagement portion 320 may be integral with one another, with an aperture 327 therebetween configured to allow a portion of plunger portion 330 to pass the rethrough.

Still referring to FIG. 3, plunger portion 330 includes an inner plunger 331 and an outer plunger 332. Inner plunger 331 may include a transverse channel that houses a pin 333 that couples inner plunger 331 to outer plunger 332, the pin 331 extending through aperture 327 of inner engagement member 320 and rotationally coupling plunger portion 330 to inner engagement portion 320. Inner plunger 331 is at least partially positioned within inner engagement portion 320. A proximal end of inner plunger 331 may be narrowed to fit within spring 325. Outer plunger 332 is positioned between inner engagement portion 320 and outer engagement portion 310. A proximal end of outer plunger 332 may include grooves extending along the outer circumference thereof, the grooves configured to mate with grooves 345 of distal clicking portion 341 when the grooves contact one another. Plunger portion 330 is shown in FIG. 3B in an unengaged condition, where plunger portion 330 is not engaged with strut 20 and the pair of grooves are also unengaged. In this unengaged condition, the distal end of inner plunger 331 extends into cavity 321 of inner engagement portion 320. The proximal end of outer plunger 332, including the grooves thereon, are spaced apart from grooves 345 of distal clicking portion 341. In this configuration, rotation of inner engagement portion 320 and plunger portion 330 may be independent of rotation of outer engagement portion 310 and distal clicking portion 341. The structure and function of certain components of driver portion 300 are described in greater detail below in the context of the use of tool 100.

Figure 4:
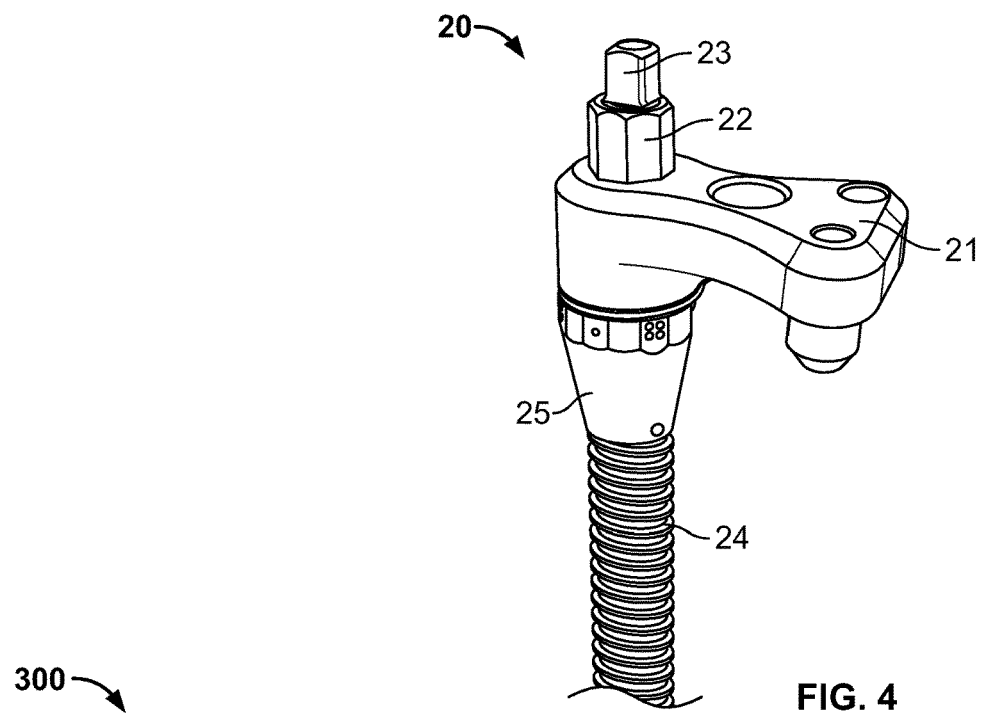
FIG. 4 is a partial perspective view of a strut of the external fixation frame of FIG. 1.

FIG. 4 illustrates an enlarged view of a proximal portion of a strut 20. As noted above, strut 20 may include a flange 21 with a plurality of apertures for facilitating attachment to a ring of external fixation frame 10. An anti-rotation/counter torque component 22 extends proximally from flange 21. Anti-rotation/counter torque component 22 is rotationally fixed to flange 21, which is in turn rotationally fixed to a ring of fixation frame 10. As shown, anti-rotation/counter torque component 22 has an octagonal shape, but any shape which provides for keyed engagement with a tool is suitable, including square or hexagonal, for example. Head of strut 20 extends proximally of anti-rotation/counter torque component 22. Head 23 is illustrated as having a square shape, but any shape which provides for keyed engagement with a tool is suitable, including hexagonal or octagonal, for example. Head 23 is operably coupled to threaded shaft 24 of strut 20. Rotation of head 23 causes rotation of threaded shaft 24. The threaded shaft 24 may extend within housing 25 and the body of flange 21, where it operably couples to head 23, which extends through an interior of anti-rotation/counter torque component 22. As noted above, although this particular strut 20 is a fixed length strut that is threaded substantially along its entire length, other struts such as telescopic struts, for example, could include a shaft into which the threaded shaft enters to change the effective length of the strut. Such telescopic struts may include similar or identical proximal portions, such as head 23, anti-rotation/counter torque component 22, flange 21, and housing 25.

Figure 5:
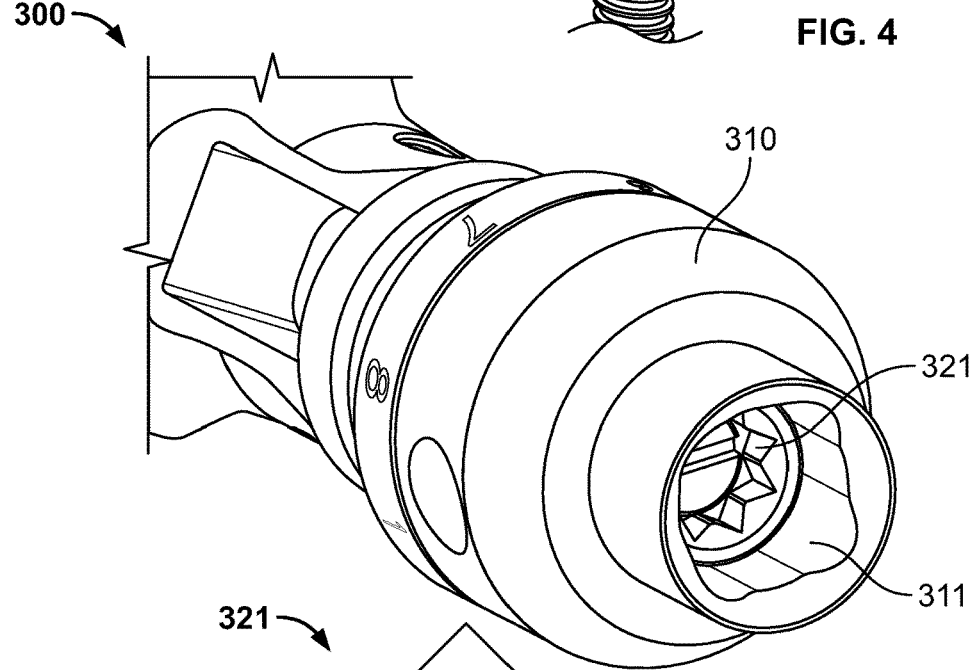
FIG. 5 is a perspective view of a distal end of the driving portion of FIG. 3.
Figure 6:
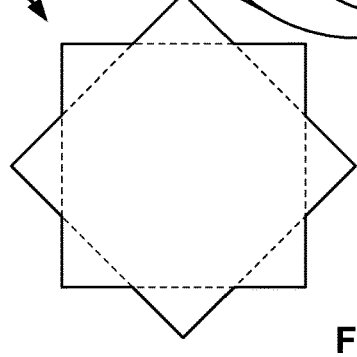
FIG. 6 is a schematic representation of cavity of an inner engagement portion of the driving portion of FIG. 5.

FIG. 5 shows an enlarged perspective view of the terminal end of driver portion 300 of tool 100. The distal end of outer engagement portion 310 is configured to mate with anti-rotation/counter torque component 22. In particular the distal end of outer engagement portion 310 has an internal square shape defining a square cavity 311. When the square cavity 311 of outer engagement portion 310 mates with the anti-rotation/counter torque component 22, the outer engagement portion 310 cannot rotate with respect to the anti-rotation/counter torque component 22 because of the keyed engagement between the corresponding square and octagonal shapes. In other embodiments, the distal end of outer engagement portion 310 may have a different shape that is keyed to the anti-rotation/counter torque component 22, such as an octagonal shape. The distal end of inner engagement portion 320 includes a shape defining a recess or cavity keyed to the shape of the head 23 of strut 20. In the illustrated embodiment, the distal end of inner engagement portion 320 is shaped to define an eight-pointed star cavity 321. In other words, the eight-pointed star cavity 321 has eight pointed grooves extending in a circumferential pattern, each groove having a substantially equal spacing between adjacent grooves. In other embodiments, the distal end of inner engagement portion 320 may have other shapes keyed to the head 23 of strut 20, such as a square. The eight-pointed star recess 321, the shape of which is illustrated in FIG. 6, is preferably composed of two individual square shapes rotated about 45 degrees with respect to one another. Each square shape is keyed to the head 23 of strut 20, so that distal end of inner engagement portion 320 can engage head 23 in eight different rotational positions.

FIGS. 7-10B illustrate different stages of engagement between tool 100 and strut 20. The initial engagement in which tool 100 is placed adjacent strut 20 is shown in FIG. 7. As shown in FIG. 7, the distal end of outer engagement portion 310 is passed over the head 23 of strut 20 until it is adjacent to anti-rotation/counter torque component 22, with the distal end of internal engagement portion 320 positioned adjacent the head 23 of strut 20. In this configuration there is no active engagement between tool 100 and strut 20.

Figure 8:
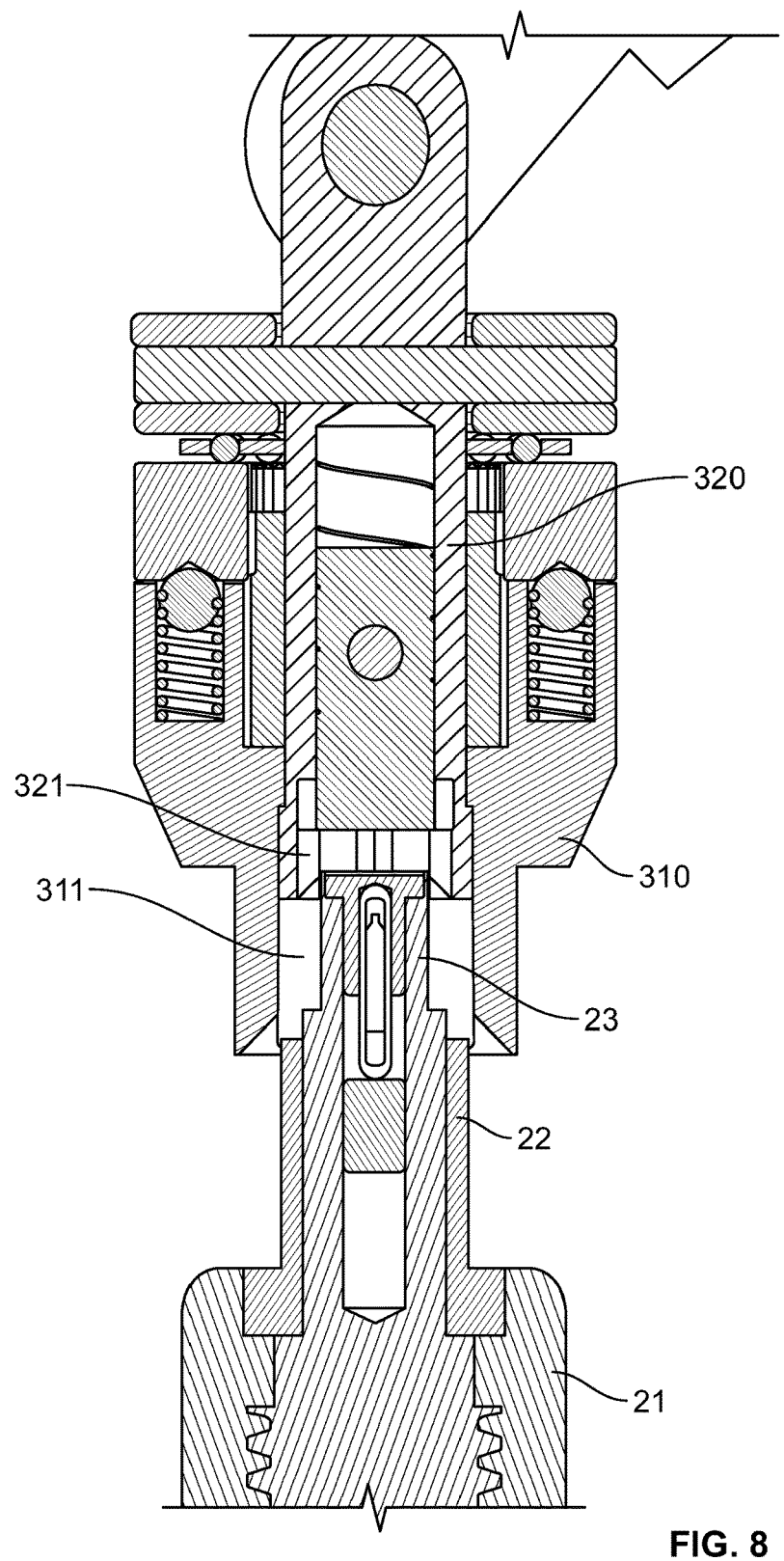
FIGS. 8-9 are cross-sections of the tool of FIG. 2 engaged with the strut of FIG. 4 in stages of further engagement.

FIG. 8 shows tool 100 pressed further down onto strut 20. In particular, the eight-pointed cavity 321 at the distal end of inner engagement portion 320 beings to engage the square head 23 of strut 20, but the cavity 311 of the outer engagement portion 310 has not yet engaged the octagonal anti-rotation/counter torque component 22 of strut 20. At this point, the outer engagement portion 320 is still free to rotate with respect to the anti-rotation/counter torque component 22 strut 20.

Figure 9:
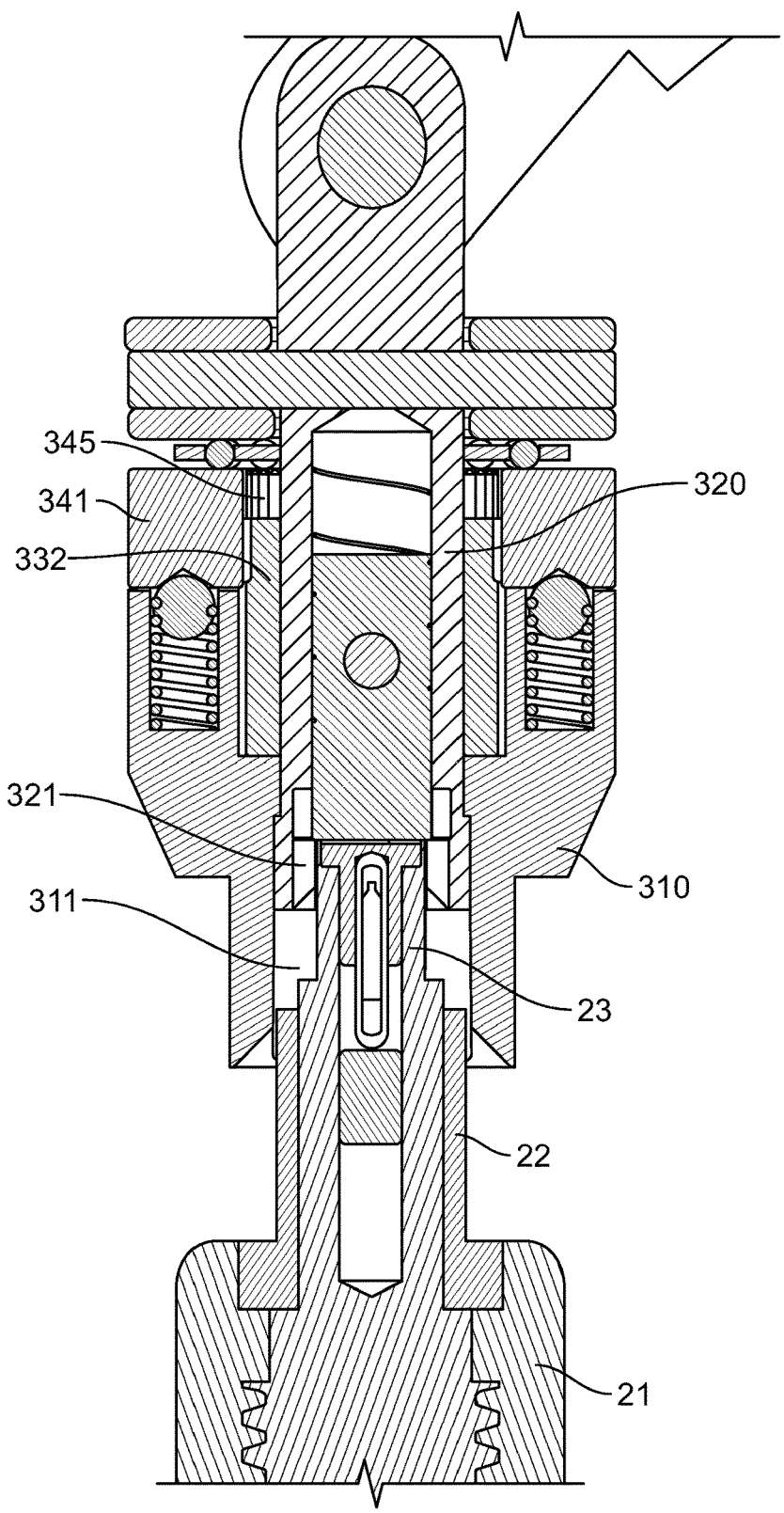

FIG. 9 shows tool 100 pressed still further down onto strut 20. As tool 100 is advanced from the position shown in FIG. 8 to the position shown in FIG. 9, the cavity 311 of outer engagement portion 310 self-rotates, if necessary, to align with anti-rotation/counter torque component 22 because the outer engagement portion 310 is free to rotate with respect to anti-rotation/counter torque component 22 until it engages the anti-rotation/counter torque component 22. In this position, the outer engagement portion 310 is rotationally locked to anti-rotation/counter torque component 22, with the inner engagement portion 320 rotationally locked to the head 23 of strut 20. However, rotation of inner engagement portion 320 in this position will not be translated to distal clicking portion 341, because the grooves on the outside of the outer plunger 332 of plunger portion 330 have not yet engaged the grooves 345 on the inside of distal clicking portion 341. The ability to self-rotate to appropriately engage the head 23 and the anti-rotation/counter torque component 22, without engaging the clicking mechanism 340, may help reduce accuracy errors caused by unintentional rotation of the head 23 relative to the anti-rotation/counter torque component 22. For example, because head 23 is free to rotate with respect to the anti-rotation/counter torque component 22, unintentional rotation may occur, for example via micromotion due to vibrations in the system. If this self-rotating feature was lacking, the head 23 would otherwise be required to be rotated with respect to the anti-rotation/counter torque component 22 in order to appropriately engage both the outer engagement portion 310 and inner engagement portion 320.

Figure 10A:
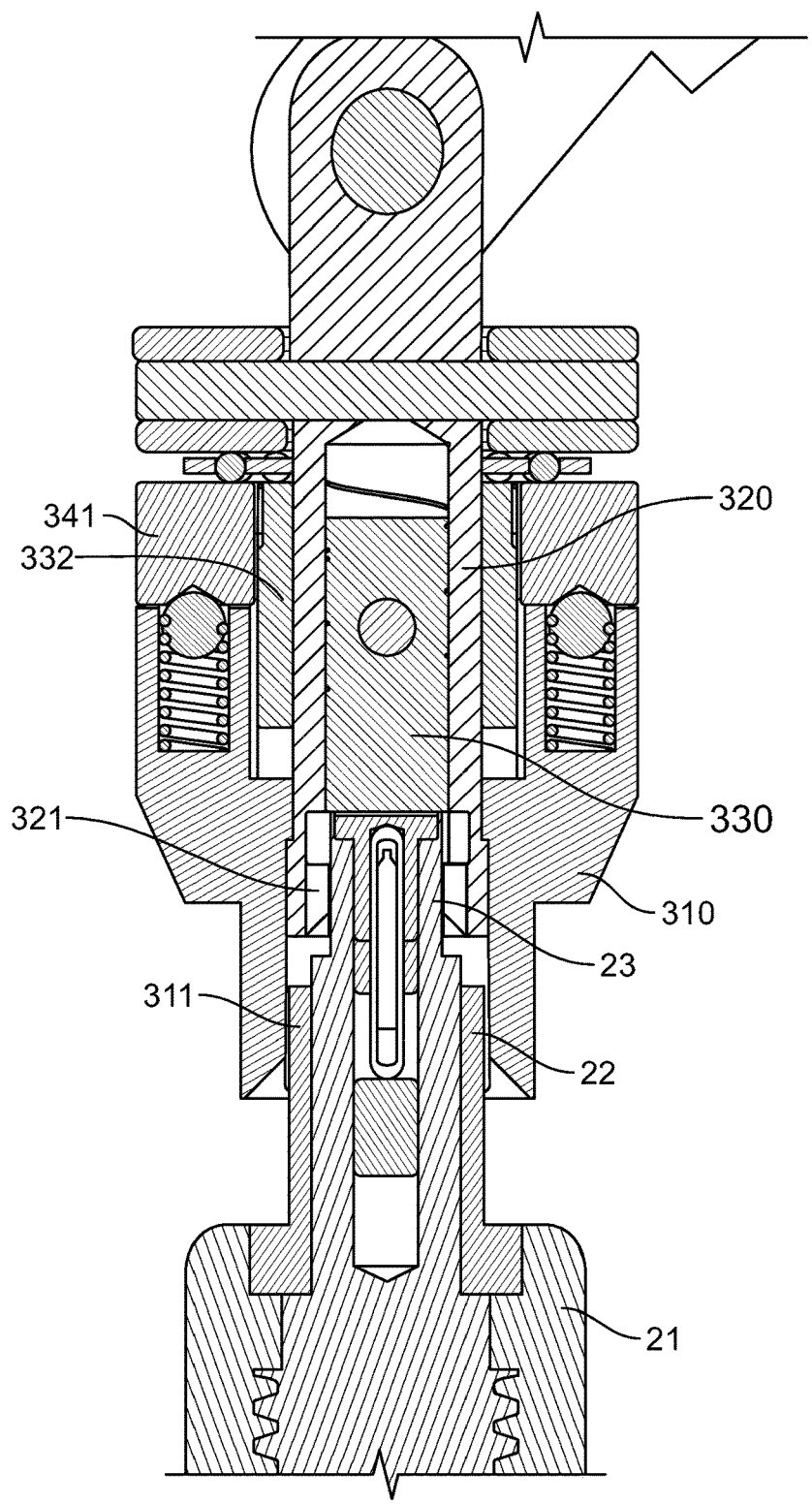
FIG. 10A is a cross-section of the tool of FIG. 2 engaged with the strut of FIG. 4 in a fully engaged condition.
Figure 10B:
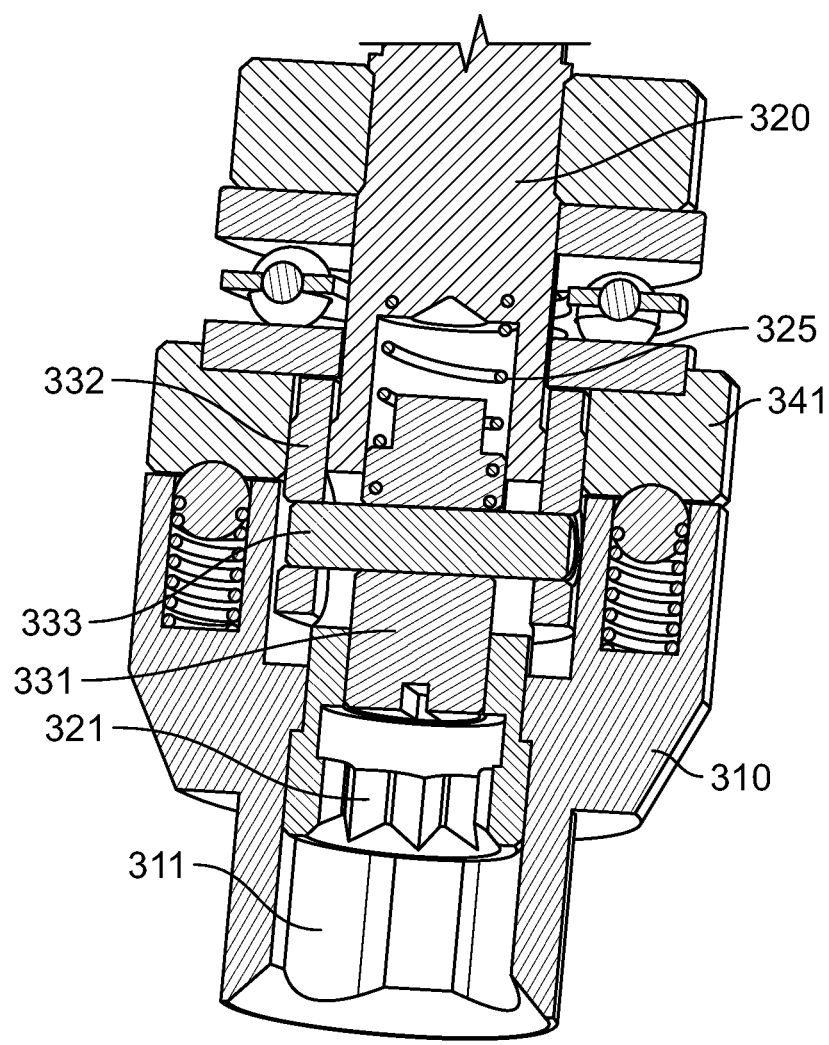
FIG. 10B is a cross-section of the driving portion in the condition shown in FIG. 10A with the strut omitted.

FIG. 10A shows tool 100 advanced further than shown in FIG. 9, with tool 100 pressed into full engagement with strut 20. FIG. 10B shows driver portion 300 in greater detail in this position with strut 20 omitted from the illustration. As tool 100 is transitioned from the position shown in FIG. 9 to the position shown in FIGS. 10A-B, the proximal end of head 23 of strut 20 pushes plunger portion proximally, compressing spring 325. As the plunger portion 330 moves proximally, the grooves on the outer circumference of the outer plunger 332 frictionally engaged the grooves 345 on the inside circumference of distal clicking portion 341, rotationally locking the plunger portion 330 to distal clicking portion 341.

In the fully engaged position shown in FIGS. 10A-B, the user may rotate tool 100, for example by manually rotating handle portion 200. Torque on the handle portion 200 is transmitted to inner engagement portion 320 via pin 230. Because the cavity 321 of inner engagement portion 320 is disposed on, and geometrically keyed with, the head 23 of strut 20, rotation of the handle portion 200 causes rotation of the strut 20. For telescopic struts, rotation of the strut 20 causes an adjustment in length of the strut 20. Further, because outer engagement portion 310 is disposed on, and geometrically keyed with, anti-rotation/counter torque component 22, the outer engagement portion 310 remains stationary during rotation of handle portion 200. Still further, rotation of inner engagement portion 320 causes rotation of plunger portion 330 due to the connection provided by pin 333. Since the grooves of outer plunger 332 are engaged with grooves 345 of distal clicking portion 341, rotation of plunger portion 330 causes rotation of distal clicking portion 341. When enough torque is provided, distal clicking portion 341 overcomes the force provided by springs 313 and balls 314, allowing distal clicking portion 341 to rotated with respect to outer engagement portion 310, until the adjacent recesses 344 engage the spring 313 and ball 314, resulting in an audible "click" and tactile feedback indicating that a ⅛ rotation of strut 20 has been completed. As should be clear, other numbers of recesses 344 may be provided to correspond to an indication of a different amount of rotation per "click." As best illustrated in FIGS. 2 and 5, distal clicking portion 341 may include visual indicia, such as numbers, to facilitate a user in keeping track of how many increments of rotation have been accomplished.

In one exemplary use of tool 100 with external fixation frame 10, a surgeon will install external fixation frame 10, including rings 12, 14, and 16 to bones B1, B2, B3 of a patient. Based on the surgeon's experience and/or instructions and/or software provided with the fixation frame 10, a correction schedule may be provided to the patient. The correction schedule may outline, for example, how much each strut 20 should be rotated during different intervals. The amount of rotation per strut 20 may be expressed in "clicks" or other discrete numbers corresponding to the amount of rotation that occurs as the distal clicking portion 341 of tool 100 disengages springs 313 and balls 314 until the adjacent recesses 344 of distal clicking portion 341 re-engage the springs 313 and balls 314. The intervals may be any desired intervals, for example strut rotations per day, or per half-day, quarter-day, etc.

As the user rotates struts 20 with tool 100 according to the correction schedule, the middle ring 14 moves up or down and may rotate with respect to the top ring 12 and bottom ring 16, moving the bone fragment B2 in the desired fashion. With other external fixators, such as those incorporating telescopic struts, rotating the struts using tool 100 increases or decreases the lengths of the struts, changing the positions of the rings with respect to one another, according to the correction schedule.

Tool 100 may be devoid of any type of motor or other electronic components, which may simplify the use of the tool 100 and reduce the cost and complexity of the tool 100. In addition, rather than have each individual strut 20 include a mechanism that provides audible, tactile, and/or visual feedback regarding the amount of rotation of the strut, the features described above in connection with tool 100 provide for such feedback, simplifying the complexity and cost of the struts 20 of fixation frame 100. The user may adjust the struts 20 using tool 100 according to the correction schedule from home, and check in with a medical personnel to confirm that the deformity correction is progressing in a satisfactory manner.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A tool for actuating one or more of a plurality of struts of an external fixation frame comprising:
   a handle portion; and
   a driving portion coupled to the handle portion, the driving portion having an inner engagement portion configured to directly couple to a movable portion of each of the struts, an outer engagement portion configured to directly couple to a non-movable portion of each of the struts, and a feedback mechanism coupled to the inner and outer engagement portions;
   wherein in a first partially engaged condition of the tool, rotation of the inner engagement portion with respect to the outer engagement portion does not cause the feedback mechanism to rotate with respect to the outer engagement portion; and wherein in a second fully engaged condition of the tool, rotation of the inner engagement portion with respect to the outer engagement portion does cause the feedback mechanism to rotate with respect to the outer engagement portion so that the feedback mechanism provides audible or tactile feedback regarding an amount of rotation of the inner engagement portion with respect to the outer engagement portion, wherein the inner engagement portion is at least partially received within the outer engagement portion.

2. The tool of claim 1, wherein the movable portion of each strut is a rotatable portion, and the feedback mechanism is rotatable with respect to both the inner and outer engagement portions.

3. The tool of claim 1, further comprising a plunger having an inner portion positioned at least partially within the inner engagement portion, and an outer portion positioned at least partially between the inner engagement portion and the outer engagement portions, the plunger being axially translatable with respect to the inner and outer engagement portions.

4. The tool of claim 3, wherein the feedback mechanism has a first mating structure and the outer portion of the plunger has a second mating structure corresponding to the first mating structure.

5. The tool of claim 4, wherein the plunger has a first axial position in the partially engaged condition of the tool in which the first mating structure is disengaged with the second mating structure, and a second axial position in the fully engaged condition of the tool in which the first mating structure is engaged with the second mating structure, the plunger being rotationally fixed with respect to the feedback mechanism when the plunger is in the second axial position.

6. The tool of claim 5, wherein the outer engagement portion includes at least one ball detent mechanism and the feedback mechanism includes a plurality of recesses configured to engage the at least one ball detent mechanism.

7. The tool of claim 4, wherein the first mating structure of the feedback mechanism and the second feedback structure of the outer portion of the plunger are both grooves.

8. An external fixation frame system comprising:
a first ring;
a second ring;
at least three struts configured to couple the first ring to the second ring, each strut having a rotatable head portion and a counter torque portion; and
an adjustment tool including a handle portion, a driver portion having an inner engagement portion for directly engaging the head portion of the strut, an outer engagement portion for directly engaging the counter torque portion of the strut, and a feedback mechanism rotatably coupled to the inner and outer engagement portions, wherein in a first partially engaged condition of the tool, rotation of the inner engagement portion with respect to the outer engagement portion does not cause the feedback mechanism to rotate with respect to the outer engagement portion; and wherein in a second fully engaged condition of the tool, rotation of the inner engagement portion with respect to the outer engagement portion does cause the feedback mechanism to rotate with respect to the outer engagement portion so that the feedback mechanism provides audible or tactile feedback regarding an amount of rotation of the inner engagement portion with respect to the outer engagement portion, wherein the inner engagement portion is at least partially received within the outer engagement portion.

9. The external fixation frame system of claim 8, wherein the tool is devoid of motors and electronic components.

10. The external fixation frame system of claim 8, wherein the tool further comprises a plunger having an inner portion positioned at least partially within the inner engagement portion, and an outer portion positioned at least partially between the inner engagement portion and the outer engagement portions, the plunger being axially translatable with respect to the inner and outer engagement portions.

11. The external fixation frame system of claim 10, wherein the feedback mechanism has a first mating structure and the outer portion of the plunger has a second mating structure corresponding to the first mating structure.

12. The external fixation frame system of claim 11, wherein the plunger has a first axial position in the partially engaged condition of the tool in which the first mating structure is disengaged with the second mating structure, and a second axial position in the fully engaged condition of the tool in which the first mating structure is engaged with the second mating structure, the plunger being rotationally fixed with respect to the feedback mechanism when the plunger is in the second axial position.

13. The external fixation frame system of claim 12, wherein the outer engagement portion includes at least one ball detent mechanism and the feedback mechanism includes a plurality of recesses configured to engage the at least one ball detent mechanism.

14. The external fixation frame system of claim 11, wherein the first mating structure of the feedback mechanism and the second feedback structure of the outer portion of the plunger are both grooves.

* * * * *